United States Patent
Soejima et al.

(10) Patent No.: US 8,242,054 B2
(45) Date of Patent: Aug. 14, 2012

(54) PLANT GROWTH REGULATOR COMPOSITION

(75) Inventors: Hiroshi Soejima, Ebetsu (JP);
Yoshihiko Katsuragawa, Ebetsu (JP);
Toru Kitamura, Ebetsu (JP); Mitsuru Honma, Sapporo (JP); Hidetoshi Tanaka, Sapporo (JP); Tamizi Sugiyama, Chofu (JP)

(73) Assignee: Snow Brand Seed Co., Ltd., Sapporo-shi (JP)

( * ) Notice: Subject to any disclaimer, the term of this patent is extended or adjusted under 35 U.S.C. 154(b) by 2 days.

(21) Appl. No.: 12/918,407

(22) PCT Filed: Feb. 19, 2009

(86) PCT No.: PCT/JP2009/000713
§ 371 (c)(1),
(2), (4) Date: Aug. 19, 2010

(87) PCT Pub. No.: WO2009/104405
PCT Pub. Date: Aug. 27, 2009

(65) Prior Publication Data
US 2011/0009262 A1    Jan. 13, 2011

(30) Foreign Application Priority Data
Feb. 19, 2008   (JP) ................................. 2008-036905

(51) Int. Cl.
*A01N 37/44* (2006.01)
(52) U.S. Cl. ........................................ 504/147
(58) Field of Classification Search .................. None
See application file for complete search history.

(56) References Cited

U.S. PATENT DOCUMENTS

| | | | |
|---|---|---|---|
| 3,544,304 A | 12/1970 | Soper, Quentin F. | |
| 4,100,160 A * | 7/1978 | Walser | 514/400 |
| 2004/0126351 A1 | 7/2004 | Hines et al. | |
| 2004/0228884 A1 | 11/2004 | Gupta | |
| 2005/0048140 A1 | 3/2005 | Hines et al. | |
| 2006/0110415 A1 | 5/2006 | Gupta | |
| 2006/0134765 A1 * | 6/2006 | Saha et al. | 435/158 |
| 2006/0147508 A1 | 7/2006 | Gupta | |
| 2007/0092461 A1 | 4/2007 | Gupta | |
| 2007/0166255 A1 | 7/2007 | Gupta | |
| 2011/0014278 A1 * | 1/2011 | Derrieu | 424/451 |

FOREIGN PATENT DOCUMENTS

| | | |
|---|---|---|
| JP | 47 18655 | 9/1972 |
| JP | 2000 300284 | 10/2000 |
| WO | WO-2006082328 | * 8/2006 |

OTHER PUBLICATIONS

International Search Report issued May 12, 2009 in PCT/JP09/000713 Feb. 19, 2009.
Mikami, Y. et al., "Several Synthetic Hydroxy-Acids as Plant Growth Regulators", Agr. Biol. Chem., vol. 34, No. 6, pp. 977-979 (1970).
Valerio, F. et al., "Production of Phenyllactic Acid by Lactic Acid Bacteria: an Approach to the Selection of Strains Contributing to Food Quality and Preservation", FEMS Microbiology Letters, vol. 233, pp. 289-295 (2004).
Law, D. M. "Gibberellin-Enhanced Indole-3 Acetic Acid Biosynthesis: D-Tryptophan as the Precursor of Indole-3-Acetic Acid". Physiol. Plantarium , vol. 70, pp. 626-632 (1987).
Mohamed K. M., "Organic Acids, Organic Acid Esters and Analgesic Activity of Tamarindus Indical, Fruits", Original Articles, Farmatsiya, vol. 52, No. 4. pp. 3-7 (2005).
Kyriacou, A. et al., "Combined Bioremediation and Advanced Oxidation of Green Table Olive Processing Wastewater", Process Biochemistry, vol. 40, pp. 1401-1408 (2005).
Kotsou, M. et al., "Integrated Aerobic Biological Treatment and Chemical Oxidation with Fenton's Reagent for the Processing of Green Table Olive Wastewater", Process Biochemistry, vol. 39, pp. 1653-1660 (2004).
Quayyum, H. A. et al., "Allelopathic Potential of Aquatic Plants Associated With Wild Rice: II. Isolation and Identification of Allelochemicals", Journal of Chemical Ecology, vol. 25 No. 1, pp. 221-228 (1999).
Ollagnier, S. et al., "The Role and Source of 5'-Deoxyadenosyl Radical in a Carbon Skeleton Rearrangement Catalyzed by a Plant Enzyme", FEBS Letters, vol. 437, pp. 309-312 (1998).
Shilling, D.C. et al., "A Rapid Seedling Bioassay for the Study of Allelopathy", Chapter 31, ACS Symposium Series, pp. 334-342, (1987).
Zauner, V. E. at al., "Hemmwirkung Von Nebenkomponenten Der Ruebenmelasse Und Von Pflanzenschutzmitteln Auf Die Atmung Und Gaerung Von Hefe (*Saccharomyces cerevisiae*)", Die Branntweinwirtschaft, vol. 119, No. 9 pp. 154-156, 158-160 and 163 (1979).
Tamura, S. "Plant Growth Regulators Produced by Microorganisms", Adv. Pestic Sci., Plenary Lect. Symp. Pap. Int. Congr. Pestic. Chem., 4th Meeting, vol. 2, pp. 356-365 (1979).
Kimura, Y. et al,, "Isolation of L-β-Phenyllactic Acid and Tyrosol as Plant Growth Regulators From Gloeosporium Laeticolor", Agr. Biol. Chem., vol. 37, No. 12, p. 2925 (1973).
"Isolation of L-β-Phenyllactic Acid as a Plant Growth-Regultilor Produced by Exobasidium", Agr. Biol. Chem., vol. 29 No. 11 pp. 1061-1062, (1965).

* cited by examiner

*Primary Examiner* — Alton Pryor
(74) *Attorney, Agent, or Firm* — Oblon, Spivak, McClelland, Maier & Neustadt, L.L.P.

(57) ABSTRACT

Provided is a plant growth regulator composition.
The plant growth regulator composition contains phenyllactic acid or a salt thereof and tryptophan or a salt thereof.

4 Claims, No Drawings

PLANT GROWTH REGULATOR COMPOSITION

CROSS-REFERENCE TO RELATED APPLICATIONS

This application is a 371 of PCT/JP09/000,713 filed Feb. 19, 2009 and claims the benefit of JP 2008-036905 filed Feb. 19, 2008.

TECHNICAL FIELD

The present invention relates to a plant growth regulator composition.

BACKGROUND ART

In the agricultural field, the control of plant growth is an important technology for improving productivity. At present, various kinds of plant growth regulators for the inhibition of plant growth are in practical use and contribute to the improvement of yield of crops and quality of products.

However, the number of plant growth regulators which promote root growth is small, and the regulators have insufficient effects and undesirable effects in many cases. For example, auxin-like substances, which are now widely used as a root promoter, may induce undesirable effects such as leaf epinasty, stem twist, stem breaking, induction of root knots, and plant death depending on the type and condition of a plant or the concentration of the compound to be applied. Therefore, the use method and use amount are limited, and the effect of promoting root growth is insufficient.

Further, in a gramineous plant such as wheat or rice, there is a problem in that, even if flowering and fertilization occurs normally, the subsequent weather condition or the like may make the progress of ripening insufficient, resulting in a decrease in yield. However, the number of plant growth regulators for improving such phenomenon is small, and the effects of the regulators are insufficient.

Meanwhile, phenyllactic acid is known to have a root promoting effect on plants (Non-patent Document 1), but the effect is weak. Therefore phenyllactic acid itself is not in practical use as a plant growth regulator. In addition, phenyllactic acid produced by a lactic acid bacterium (*Enterococcus faecalis*) has been reported to have antibacterial activity (Patent Document 1).

Moreover, tryptophan has been reported to serve in a specific tissue of a specific plant as a precursor of indoleacetic acid which is a plant hormone (Non-patent Document 2). However, in general, such effect is not provided, and the compound is not in practical use as a plant growth regulator.
Patent Document 1: JP-A-2000-300284
Non-patent Document 1: Mikami et al. 1970. Several synthetic hydroxy-acids as plant growth regulators. Agricultural and Biological Chemistry 34: 977-979.
Non-patent Document 2: Law 1987. Gibberellin-enhanced indole-3-acetic acid biosynthesis: D-Tryptophan as the precursor of indole-3-acetic acid. Physiol. Plant. 70: 626-632.

DISCLOSURE OF THE INVENTION

Problems to be Solved by the Invention

Therefore, an object of the present invention is to provide a plant growth regulator having a root promoting effect on plants or a ripening effect on gramineous plants.

Means for Solving the Problems

The inventors of the present invention have made extensive studies to solve such problems. As a result, surprisingly, the inventors have found that the combination use of phenyllactic acid and tryptophan significantly enhances the root promoting effect on plants or ripening effect on gramineous plants, and thus completed the present invention.

Accordingly, the present invention provides a plant growth regulator composition containing phenyllactic acid or a salt thereof and tryptophan or a salt thereof.

The present invention also provides a method of regulating plant growth, including applying phenyllactic acid or a salt thereof and tryptophan or a salt thereof to a plant.

Effects of the Invention

The plant growth regulator composition of the present invention has high root promoting activity on plants and has very low side-effects such as leaf epinasty promoting effect. Therefore, the composition may be used as a plant growth regulator, in particular, as a root promoter during the whole growth period. In particular, the composition is useful as a root promoter in the seedling raising period and at the time of transplantation. Moreover, the composition is useful as a ripening improver which promotes the growth of the grains of gramineous plants. In addition, because the composition has high root promoting activity on plants, the composition is useful as a pesticide or a fertilizer additive. The composition itself is also useful as a fertilizer.

BEST MODES FOR CARRYING OUT THE INVENTION

Active ingredients of the plant growth regulator composition of the present invention (hereinafter, referred to as "plant growth regulating substances") are phenyllactic acid or a salt thereof and tryptophan or a salt thereof.

Of the plant growth regulating substances to be used in the present invention, tryptophan may be D-form, L-form, or a mixture thereof but is preferably L-form.

The tryptophan may be a commercially available product or a product obtained by organic synthesis or microorganism fermentation. In addition, tryptophan may be a composition containing tryptophan or a salt thereof, and examples of the composition include a microorganism fermentation culture containing tryptophan, a protein/peptide containing tryptophan as a component (so-called protein form), or a degradation product thereof. Of those, tryptophan or a salt thereof, or a culture containing tryptophan or a salt thereof, other than the protein form, is particularly preferred.

As a method of producing tryptophan, there is exemplified a method of Oki et al. including industrially synthesizing DL forms of tryptophan and resolving the products to obtain D-form and L-form (Oki et al. (ed.), "Chemical Dictionary" Tokyo Kagaku Dojin). Meanwhile, L-form can be obtained by a fermentation method or a microbial conversion method using a microorganism, or by an enzymatic method using an enzyme derived from a microorganism (Isamu Shiio, 1986, Tryptophan, phenylalanine, tyrosine fermentation, Aida et al. (ed.), "Amino acid fermentation" pp. 343-360, Japan Scientific Societies Press).

Of the plant growth regulating substances to be used in the present invention, phenyllactic acid (3-phenyllactic acid) may be D-form, L-form, or a mixture thereof but is preferably D-form.

The phenyllactic acid may be a commercially available product or a product obtained by organic synthesis or microorganism fermentation.

In addition, the plant growth regulating substance may be a composition containing phenyllactic acid or a salt thereof, and examples of the composition include vinegar. As described in Examples below, cultures of phenyllactic acid-producing microorganisms such as corn steep liquor contain phenyllactic acid, and the inventors have clarified that those cultures can be used as plant growth regulating substances. Therefore, the substances may be used without additional treatment or may be concentrated, diluted, or suspended before use. In this case, it goes without saying that, in the production of corn steep liquor, a lactic acid bacterium having high phenyllactic acid-producing ability is desirably inoculated.

Phenyllactic acid may be obtained by pyrolyzing a diazonium salt obtained by diazotizing phenylalanine in an acidic aqueous solution (Kimura and Tamura 1973. Isolation of L-β-phenyllactic acid and tyrosol as plant growth regulators from *Gloeosporium laeticolor*. Agricultural and Biological Chemistry 37: 2925). Moreover, phenyllactic acid may be obtained by so-called van Slyke method including dissolving phenylalanine in sulfuric acid and adding sodium nitrite thereto (Koga et al. 1971. Examinations on the neighboring aryl group participation in nitrous acid deaminations of L-phenylalanine and its p-nitro and p-methoxy derivatives. Tetrahedron Lett. 25: 2287-2290).

Further, phenyllactic acid may be obtained by culturing a phenyllactic acid-producing microorganism in a generally used medium. The medium to be used in this case may be a generally used medium (such as MRS medium or GYP medium) as well as a corn extract. In addition, if the amount of phenylalanine as a substrate of phenyllactic acid (The Chemical Society of Japan (ed.), 1997, "Cell function and metabolism maps (I)" Tokyo Kagaku Dojin) to be added to a medium is increased, the amount of phenyllactic acid to be obtained may be increased.

Examples of the microorganism include lactic acid bacteria such as *Lactobacillus* bacteria and *Enterococcus* bacteria, and the *Lactobacillus* bacteria are preferred. Specifically, examples of the *Lactobacillus* bacteria include *Lactobacillus rhamnosus* and *Lactobacillus plantarum* (Valerio et al. 2004. Production of phenyllactic acid by lactic acid bacteria: an approach to the selection of strains contributing to food quality and preservation. FEMS Microbiol. Lett. 233: 289-295), and examples of the *Enterococcus* bacteria include *Enterococcus faecalis* (JP-A-2000-300284) Of those, *Lactobacillus rhamnosus* and *Lactobacillus plantarum*, in particular, *Lactobacillus rhamnosus* (FERM P-13245) strain, *Lactobacillus plantarum* (FERM P-18930) strain, and *Lactobacillus plantarum* N strain are preferred. Of those, the former two strains were deposited with International Patent Organism Depositary, National Institute of Advanced Industrial Science and Technology (address: Central 6, Higashi 1-1-1, Tsukuba-shi, Ibaraki-ken) on Nov. 6, 1992 and on Jul. 9, 2002, respectively.

In addition, corn steep liquor is one of by-products in the production of corn starch, and the production process includes lactic acid fermentation (Taizo Miwa, 1979. Corn processing industry by-products. "Formula Feed Lecture (second volume)" pp. 265-269. Chikusan Publishing Co., Ltd.).

In addition, vinegar is known to contain phenyllactic acid, and vinegar may be used.

In addition, the above-mentioned culture containing phenyllactic acid may be treated with an ion-exchange resin, a porous synthetic adsorbent, solvent extraction, or the like to partially purify or purify and to isolate phenyllactic acid before use.

For example, a partially purified product of corn steep liquor may be obtained by adjusting pH of an aqueous corn steep liquor solution to a neutral range (pH 5 to 8), performing adsorption on a strongly basic ion-exchange resin or a weakly basic ion-exchange resin, and performing elution with an aqueous alcohol solution containing an acid. In this process, the ion-exchange resin before adsorption is preferably converted to the formate form or the acetate form.

The concentration of the acid in the solution is preferably 0.01 to 4 N, more preferably 1 to 3 N. Examples of the acid include formic acid, acetic acid, hydrochloric acid, and sulfuric acid.

The concentration of the alcohol in the solution is preferably 0 to 80% by volume, more preferably 10 to 30% by volume. Examples of the alcohol include methanol, ethanol, butanol, and isopropanol.

In addition, for example, the partially purified product of corn steep liquor may be obtained by adjusting pH of an aqueous corn steep liquor solution to an acidic range (pH 1 to 4), performing adsorption on a polystyrene-based synthetic adsorbent, a styrene-divinylbenzene-based adsorbent, or a methacrylate-based synthetic adsorbent, and performing elution with an aqueous alcohol solution or an aqueous ketone solution.

The concentration of the alcohol or the ketone in the solution is preferably 0 to 99% by volume, more preferably 10 to 30% by volume. Examples of the alcohol include methanol, ethanol, butanol, and isopropanol. The ketone includes acetone or the like.

Note that, in the case where a culture of a phenyllactic acid-producing microorganism contains tryptophan or a salt thereof, the culture may be used without additional treatment as the plant growth regulator composition of the present invention. However, in the case where the content of tryptophan or a salt thereof in the culture is small, tryptophan or a salt thereof may further be added.

In addition, examples of the salt of phenyllactatic acid or tryptophan include, without any particular limitation: salts with alkali metals such as sodium and potassium; salts with alkaline earth metals such as calcium and magnesium; an ammonium salt; organic acid salts such as a citrate, a tartrate, an oxalate, a lactate, and an acetate; mineral acid salts such as a phosphate, a carbonate, a nitrate, a sulfate, and a hydrochloride.

The content ratio of phenyllactic acid or a salt thereof and tryptophan or a salt thereof in the plant growth regulator composition of the present invention is, in terms of mass ratio, preferably 1:700 to 99:1, more preferably 1:600 to 99:1, still more preferably 1:500 to 99:1, yet still more preferably 1:200 to 9:1, particularly preferably 1:50 to 9:1 in view of the plant growth regulating effect or enhancing effect of the combination use of the two components. In this case, a solution preferably contains phenyllactic acid or a salt thereof at a concentration of 0.1 ppm or more and tryptophan or a salt thereof at a concentration of 1 ppm or more.

The plant growth regulator composition of the present invention may be produced by mixing, stirring, or the like, the above-mentioned plant growth regulating substances and other optional components in accordance with a conventional method.

While the plant growth regulator composition of the present invention may be a mixture of the above-mentioned plant growth regulating substances itself, the composition may be formulated with a carrier which is used for a general plant growth regulator, such as wettable powder, emulsion, granule, or powder.

The form of the formulation is not particularly limited, and the composition may be formed into any formulation form such as powder, granulated powder, granule, wettable powder, flowable, emulsion, and paste.

As a solid carrier, for example, mineral powders (such as kaolin, bentonite, clay, montmorillonite, talc, diatom earth, mica, vermiculite, gypsum, calcium carbonate, and monocalcium phosphate), vegetable powders (such as soy powder, flour, wood powder, tobacco powder, starch, and crystalline cellulose), polymers (such as a petroleum resin, a polyvinyl alcohol resin, a polyvinyl acetate resin, polyvinyl chloride, and a ketone resin), and further, alumina, waxes, or the like each can be used. In addition, as a liquid carrier, for example, alcohols (such as methanol, ethanol, propanol, butanol, ethylene glycol, and benzyl alcohol), aromatic hydrocarbons (such as toluene, benzene, and xylene), chlorinated hydrocarbons (such as chloroform, carbon tetrachloride, and monochlorobenzene), ethers (such as dioxane and tetrahydrofuran), ketones (such as acetone, methyl ethyl ketone, and cyclohexane), esters (such as ethyl acetate and butyl acetate), acid amides (such as N,N-dimethylacetamide), ether alcohols (such as ethylene glycol ethyl ether), water, or the like each can be used.

A surfactant to be used for emulsification, dispersion, or diffusion may be nonionic, anionic, cationic, or amphoteric. Examples of the surfactant which can be used in the present invention include polyoxyethylene alkyl ethers, polyoxyethylene alkylaryl ethers, polyoxyethylene fatty acid esters, sorbitan fatty acid esters, polyoxyethylene sorbitan fatty acid esters, polyoxyethylene sorbitol fatty acid esters, glycerin fatty acid esters, oxyethylene polymers, oxypropylene polymers, polyoxyethylene alkyl phosphoric acid esters, fatty acid salts, alkyl sulfuric acid ester salts, alkyl sulfonic acid salts, alkylaryl sulfonic acid salts, alkyl phosphoric acid salts, alkyl phosphoric acid ester salts, polyoxyethylene alkyl sulfuric acid esters, quaternary ammonium salts, oxyalkylamines, lecithins, and saponins. Gelatin, casein, sodium alginate, starch, agar, polyvinyl alcohol, or the like can be used as an auxiliary substance, as required.

The pH (25° C.) of an aqueous solution or suspension of the plant growth regulator composition of the present invention is preferably 2 to 8, and a buffer to adjust the pH includes: an organic acid such as an acetate, a citrate, a fumarate, a malate, a lactate, a gluconate, or a tartrate; an inorganic acid such as a phosphate, a hydrochloride, or a sulfate; a hydroxide such as sodium hydroxide; and ammonia or ammonia water. The buffers may be used singly or in combination of two or more kinds of them or may be appropriately combined with another pH adjuster.

While the plant growth regulator composition of the present invention has an effect of increasing the amount of roots, an effect of promoting overall growth and the like, the composition is particularly preferably used as a root promoter or a ripening improver for gramineous plants.

Moreover, the plant growth regulator composition of the present invention contains amino acids, and hence the composition itself may be used as a fertilizer.

In the case where the plant growth regulator composition of the present invention is applied to a plant, the composition may be used directly without additional treatment, or diluted or suspended with water to a predetermined concentration before use.

Meanwhile, phenyllactic acid or a salt thereof and tryptophan or a salt thereof may be separately prepared as different formulations, and the formulations may be simultaneously applied to a plant.

In the case where the composition is applied to a plant, the composition may be used as an agent for soil treatment, an agent for foliage treatment, an agent for seed treatment before sowing, an agent for the treatment of plant before transplantation, an agent for the treatment of a plant in transplantation, or the like. In addition, in the case of hydroponic culture, the composition may be mixed in a hydroponic solution before use, while the composition may be suspended or dissolved in a medium in the case of tissue culture.

As for the concentration of the plant growth regulator composition of the present invention used for spraying, the total concentration of phenyllactic acid or a salt thereof and tryptophan or a salt thereof can be in a range of preferably 0.01 to 100,000 ppm, more preferably 1 to 10,000 ppm, particularly preferably 5 to 1000 ppm. In particular, in the case where the composition is used for seedlings in the seedling raising period, a diluted solution of the above-mentioned concentration is desirably sprayed in an amount of 50 to 200 mL per L of culture soil. Meanwhile, in the case where the composition is used as a ripening improver for gramineous plants, the solution is desirably sprayed in an amount of 200 to 2000 L per ha of a land area. In these cases, a spreading agent may be used, and the type and amount of the spreading agent to be used are not particularly limited.

As for the amount of the composition used in the case of direct application to soil, including the case of mixing with a fertilizer, the total concentration of phenyllactic acid or a salt thereof and tryptophan or a salt thereof is preferably 100 to 10,000 g, particularly preferably 500 to 5000 g per hectare. In particular, in the case where the composition is used for seedlings in the seedling raising period, the composition is desirably used in an amount of 0.001 to 10 g per L of culture soil. In this case, the composition may be mixed in advance into culture soil before sowing or may be sprayed during the seedling raising period.

In the case where the composition is used for treating seeds before sowing, the composition is diluted with or suspended in a liquid carrier such as water, an alcohol (such as methanol or ethanol), a ketone (such as acetone), an ether (such as diethyl ether), or an ester (such as ethyl acetate) so that the total concentration of phenyllactic acid or a salt thereof and tryptophan or a salt thereof is 0.01 to 100,000 ppm. The resultant solution may be sprayed to dried seeds, or the dried seeds may be immersed in the diluted solution so that the solution is absorbed in the seeds. The immersion time is not particularly limited, but the time is preferably 1 second to 30 minutes. The treated seeds may be subjected to air-drying, reduced-pressure drying, heat drying, or vacuum drying to evaporate the liquid carrier. Moreover, a product obtained by formulating the composition using a mineral powder solid carrier such as clay may be attached on the surfaces of seeds before use. Further, the composition may be mixed with a general seed coating agent or a general seed coating film to coat the seeds.

In the case where the composition is used in tissue culture or in cell culture, the composition may be dissolved or suspended in a general medium for plant tissue culture (such as MS medium, White medium, or Gamborg B5 medium) before use so that the total concentration of phenyllactic acid or a salt thereof and tryptophan or a salt thereof is in a range of 0.01 to 10,000 ppm, particularly preferably 0.1 to 1000 ppm. In this case, as usually performed, a sugar (such as sucrose or glucose) may be appropriately added as a carbon source; and a cytokinin (such as benzyladenine or kinetin), an auxin (such as indoleacetic acid or naphthaleneacetic acid), a gibberellin (such as GA3 or GA4), abscisic acid, and the like may be appropriately added as plant hormones.

In the case where the composition is absorbed directly in a plant before transplantation, the root or whole body of the plant may be immersed in a solution obtained by diluting or suspending the composition so that the total concentration of phenyllactic acid or a salt thereof and tryptophan or a salt thereof is 0.1 to 1000 ppm. Meanwhile in the case of scion, leaf-bud cutting, cutting, or the like, the base or whole body may be immersed. In this case, the immersion time is preferably 1 second to 1 week, particularly preferably 1 minute to 3 days. In addition, a product obtained by formulating the composition using a mineral powder solid carrier may be attached to the root, or in the case of the scion, the leaf-bud cutting, the cutting, or the like, the product may be attached to the stem base.

The plant growth regulator composition of the present invention may be applied at any time in the whole growth period. However, in particular, in the case where the composition is applied as a root promoter, the composition is particularly effectively used before sowing, during sowing, during cultivation of seedlings, before or after a process with cultural root cutting such as transplantation, or when a weather factor or the like inhibits root growth or causes a disorder in roots. Meanwhile, in the case where the composition is used as a ripening improver for gramineous plants, the composition is effectively used during the period from a flowering stage to a yellow ripe stage.

When the plant growth regulator composition of the present invention is applied to a plant as a root promoter, the number of roots such as the number of lateral roots or the number of adventitious roots increases, resulting in increasing the root amount and root density, which leads to effects such as improvement of survival rate in transplantation of seedlings, growth of healthy seedlings, promotion of growth, improvement of water absorption ability, improvement of fertilizer absorption ability, improvement of fertilizer component availability, green color retention, improvement of photosynthetic capability, improvement of water stress resistance, prevention of lodging, and increase in yield. Meanwhile, in the case where the composition is used as a ripening improver for gramineous plants, weight per grain increases, which leads to an effect such as increase in yield.

Examples of the plant to which the plant growth regulator composition of the present invention is applicable include without any particular limitation: solanaceous vegetables such as tomato, bell pepper, chili pepper, and eggplant; cucurbitaceous vegetables such as cucumber, pumpkin, melon, and watermelon; raw eaten vegetables and condiment vegetables such as celery, parsley, and lettuce; alliaceous vegetables such as Welsh onion, onion, and garlic; pulses such as soybeans, peanuts, common beans, peas, and adzuki beans; other vegetable fruits such as strawberry; axial roots such as radish, turnip, carrot, and burdock; tuber crops such as taro, cassava, potato, sweet potato, and Chinese yam; leaf vegetables such as asparagus, spinach, and Japanese honeywort; flowers and ornamental plants such as tulip gentian, stock, carnation, and mum; cereals such as rice, wheat, barley, oat, and corn; grasses such as bent grass and Korean lawn grass; oil crops such as rapeseed and sunflower; sugar crops such as sugarcane and sugar beet; fiber crops such as cotton and rush; feed crops such as clover, sorghum, and dent corn; deciduous fruit trees such as apple, pear, grape, and peach; citrus fruits such as Satsuma mandarin, lemon, and grapefruit; and woody plants such as Satsuki azalea, azalea, and Japanese Cedar.

When the plant growth regulator composition of the present invention is applied as a root promoter, the composition is particularly effective for, out of the examples: plants which are replanted during their cultivation such as tomato, bell pepper, chili pepper, eggplant, cucumber, pumpkin, melon, watermelon, celery, parsley, lettuce, Welsh onion, onion, asparagus, tulip gentian, stock, rice, bent grass, Korean lawn grass, sugar beet, and rush; and plants which reproduce by rooting from cuttings or scions such as mum, carnation, Satsuki azalea, azalea, and grape. In addition, when the plant growth regulator composition of the present invention is used as a ripening improver for gramineous plants, the composition is particularly effective for plants in which grains are not enclosed in covering such as wheat, rice, barley, and oat.

To improve the effect of the present invention, the composition may be used in combination with another plant growth regulator, and the combination use may provide a synergistic effect in some cases. For example, in the case where the composition is applied as a root promoter in raising seedling under a condition where spindly growth occurs very frequently, such as high cultivation density, high humidity, or lack of sunlight, to grow good seedlings with a small weight ratio of aerial part to underground part, the composition may be used in combination with an anti-gibberellin agent having a strong effect of inhibiting stem extension (such as paclobutrazol, uniconazole P, or ancymidol), a growth inhibitor (such as daminozide), or an ethylene-generating agent (such as ethephon). In the case of scion, leaf-bud cutting, cutting, or tissue culture, to enhance the root promoting effect, the composition may be used in combination with an auxin-like substance (such as indoleacetic acid, indolebutyric acid, naphthylacetamide, or naphthaleneacetic acid). Moreover, in a treatment of seeds before sowing, the composition may be used in combination with a gibberellin agent having a germination promoting effect. Meanwhile, in the case where the composition is used as a ripening improver for gramineous plants, the composition may be used in combination with another ripening rate improver such as hydroxyisoxazole or isoprothiolane. The compounds are shown for illustrative purposes only, and other plant growth regulators which can be used in combination with the plant growth regulator of the present invention are not limited thereto.

Further, the plant growth regulator composition of the present invention may be used by mixing with or in combination with a variety of pesticides, bactericidal agents, microbial pesticides, fertilizers, and the like. In particular, in the case where the composition is applied as a root promoter, the composition is effectively used in combination with hydroxyisoxazole, methasulfocarb, metalaxyl, or the like, which has been reported to have a root promoting effect as well as a bactericidal effect. The composition is particularly effectively used by mixing with a pesticide or a bactericidal agent used in the seedling raising period. In the case where the composition is used in combination with a fertilizer, it is particularly effective to use the composition in combination with a fertilizer for raising seedling for the purpose of growth of healthy seedlings or to use the composition in combination with a fertilizer to be applied just before transplantation for the purpose of survival promotion. Moreover, the composition is particularly effectively used by mixing with a delayed release fertilizer for the purposes of long-time duration of the effect of the plant growth regulator composition of the present invention to improve fertilizer component availability.

Meanwhile, in the case where the composition is used as a ripening improver for gramineous plants, the composition is effectively used by mixing with another fertilizer for spraying on leaf surface, such as urea, ammonium phosphate, or an amino acid.

EXAMPLES

Hereinafter, the present invention is described in more detail by way of examples. However, the present invention is not limited to the following examples.

Production Example 1

Production Method by Culture of Lactic Acid Bacterium Using Synthetic Medium

Lactic acid bacteria, *Lactobacillus rhamnosus* FERM P-13245 and *L. plantarum* FERM P-18930 strains, were inoculated into a synthetic medium (prepared by dissolving, in 1 L of distilled water, 10 g of glucose, 6 g of sodium acetate, 1 g of ammonium citrate, 3 g of potassium phosphate monobasic, 3 g of potassium phosphate dibasic, 0.5 g of magnesium sulfate heptahydrate, 0.02 g of iron sulfate heptahydrate, 0.05 g of manganese sulfate heptahydrate, 1 g of Tween 80 (registered trademark), 2 mg of pyridoxal, 1 mg of calcium pantothenate, 1 mg of riboflavin, 1 mg of nicotinic acid, 0.2 mg of p-aminobenzoic acid, 0.01 mg of biotin, 0.1 mg of folic acid, 0.1 g of L-arginine, 0.2 g of L-aspartic acid, 0.2 g of L-cysteine, 0.2 g of L-glutamic acid, 0.1 g of L-isoleucine, 0.1 g of L-leucine, 0.1 g of L-lysine, 0.1 g of L-methionine, 0.1 g of L-serine, 0.1 g of L-threonine, 0.1 g of L-tryptophan, 0.1 g of L-tyrosine, 0.1 g of L-valine, and 5 g of L-phenylalanine and sterilizing the resultant solution at 121° C. for 10 minutes in an autoclave) obtained by slightly modifying a medium developed by Morishita et al. (Morishita et al. 1981. Multiple nutritional requirements of Lactobacilli: genetic lesions affecting amino acid biosynthetic pathways. J. Bacteriol. 148: 64-71) and cultured at 27° C. for 3 days.

Partial purification was performed as follows. SepPak PS-2 (manufactured by Waters) was washed in advance with 99% methanol and conditioned with acetic acid water at pH 3.0. Each of the cultures (30 mL) was adjusted to pH 3.0 with diluted hydrochloric acid and centrifuged at 6500 rpm for 30 minutes, and the supernatant (10 mL) was passed through a cartridge adjusted to adsorb phenyllactic acid. Subsequently, the cartridge was washed with 5 mL of 1 N acetic acid water, and elution was performed with 20 mL of 40% methanol. The eluate was concentrated with an evaporator to about 500 mL, and the concentrate was adjusted to pH 8.0 with an aqueous sodium hydroxide solution, followed by extraction with ethyl acetate three times. The ethyl acetate layer was discarded. The residual aqueous layer was adjusted to pH 2.5 with hydrochloric acid, and extraction was performed with ethyl acetate three times. The resultant ethyl acetate layer was dehydrated with anhydrous magnesium sulfate, and the solvent was removed under reduced pressure. The residue was dissolved in a small amount of 10% methanol, and the solution was passed through SepPak C18 cartridge (manufactured by Waters) adjusted with 10% methanol, followed by elution with 20 mL of 10% methanol. The eluate was dried under reduced pressure.

The samples were analyzed by HPLC (column: Puresil C18, inner diameter 4.6 mm×length 250 mm (manufactured by Waters); column temperature: 40° C.; mobile phase: 40% methanol containing 1% acetic acid; flow rate: 0.8 mL/min). A peak was detected at 10.22 minutes, and the time was almost the same as that of a reagent of phenyllactic acid (Sigma-Aldrich Japan). The ultraviolet absorption spectrum of the peak was measured, and the absorption maximum was detected at 259 nm. The wavelength was the same as that of the reagent of phenyllactic acid. Peak areas measured at 260 nm were compared with a calibration curve drawn using the reagent of phenyllactic acid. The phenyllactic acid concentration in the culture of the lactic acid bacterium *Lactobacillus rhamnosus* FERM P-13425 strain-inoculated group was calculated to be 78 mg/L, and the phenyllactic acid concentration in the culture of the *L. plantarum* FERM P-18930 strain-inoculated group was calculated to be 147 mg/L.

Then, the cultures were defined as lactic acid bacterium cultures themselves, and L-tryptophan (Wako Pure Chemical Industries, Ltd.) was added to the lactic acid bacterium cultures themselves at a concentration one-tenth that of phenyllactic acid, to thereby prepare lactic acid bacterium culture/L-tryptophan mixtures.

Production Example 2

Production Method by Culture of Lactic Acid Bacterium Using Corn Extract 50 g of corn meal (Sigma-Aldrich Japan) were added to 1 L of distilled water, and extraction was performed at 85° C. for 1 hour. The resultant was centrifuged at 6500 rpm for 30 minutes, to thereby obtain a supernatant. The supernatant was sterilized in an autoclave, and the *Lactobacillus plantarum* FERN P-18930 strain was inoculated thereto and cultured at 27° C. for 4 days. The culture was analyzed in the same way as in Production Example 1, and the phenyllactic acid concentration was found to be 0.25 mg/L.

Then, the culture was defined as a corn lactic acid bacterium culture itself, and 0.025 mg of L-tryptophan (Wako Pure Chemical Industries, Ltd.) was added with respect to 1 L of the culture, to thereby prepare a corn lactic acid bacterium culture/L-tryptophan mixture.

Production Example 3

Production Method Using Corn Steep Liquor

To 1.5 L of corn steep liquor (Wako Pure Chemicals Industries, Ltd.) was added the same amount of distilled water, and the resultant was adjusted to pH 7 with sodium hydroxide. The solution was passed through a strongly basic anion-exchange resin DIAION (registered trademark) PA418 column (inner diameter 45 mm×length 550 mm) converted to the formate form to adsorb phenyllactic acid and tryptophan, and the column was washed with 1 L of distilled water, followed by elution with 2 L of a 30% isopropanol solution containing 2 N formic acid. The eluate was concentrated under reduced pressure to distill off isopropanol and adjusted to pH 3.0 with sodium hydroxide. Separately, a styrene-divinylbenzene-based synthetic adsorption resin DIAION (registered trademark) HP-20 was washed with methanol, and a column (inner diameter 45 mm×length 550 mm) was filled with the resin and adjusted with pH 3.0 acetic acid water. The above-mentioned concentrate was passed through the column to adsorb phenyllactic acid. The column was washed with 1 L of pH 3.0 acetic acid water, and phenyllactic acid was eluted with 2 L of 20% isopropanol. The eluate was concentrated to about 500 mL with an evaporator, and the concentrate was adjusted to pH 8.0 with an aqueous sodium hydroxide solution. Extraction was performed with ethyl acetate three times, and the ethyl acetate layer was discarded. The residual aqueous layer was adjusted to pH 2.5 with hydrochloric acid, and extraction was performed with ethyl acetate three times. The resultant ethyl acetate layer was dehydrated with anhydrous magnesium sulfate and dried under reduced pressure. The sample was subjected to a silica gel column (inner diameter 20 mm×length 250 mm), and the column was washed with a mixture of n-hexane:acetic acid=99:1, followed by elution with a mixture of n-hexane:ethyl acetate:acetic acid=39:60:1. The eluate was concentrated under reduced pressure, and the residue was dissolved in a small amount of 10% methanol. The solution was passed through SepPak C18 cartridge (manufactured by Waters) adjusted with 10% methanol, and elution was performed with 20 mL of 10% methanol. The eluate was dried under reduced pressure.

The sample was purified by HPLC (column: YMC C8 inner diameter 20 mm×length 250 mm (manufactured by YMC Co., Ltd.); column temperature: room temperature; mobile phase: 50% methanol containing 1% acetic acid; flow rate: 6 mL/min) to separate a fraction corresponding to phenyllactic acid (retention time: 20 to 25 min). The separated fraction was further purified by HPLC (column: YMC ODS-A inner diameter 10 mm×length 250 mm (manufactured by YMC Co., Ltd.); column temperature: room temperature; mobile phase: 45% methanol containing 1% acetic acid; flow rate: 2 mL/min) to separate a fraction corresponding to phenyllactic acid (retention time: 19 to 22 min). The separated fraction was further purified by HPLC (column: YMC Phe inner diameter 10 mm×length 250 mm (manufactured by YMC Co., Ltd.); column temperature: room temperature; mobile phase: 40% methanol containing 1% acetic acid; flow rate: 2 mL/min) to separate a fraction corresponding to phenyllactic acid (retention time: 17 to 20 min). The separated fraction was further purified by HPLC (column: YMC ODS-A inner diameter 10 mm×length 250 mm (manufactured by YMC Co., Ltd.); column temperature: room temperature; mobile phase: 40% acetonitrile containing 1% acetic acid; flow rate: 2 mL/min) to separate a fraction corresponding to phenyllactic acid (retention time: 10 to 12 min) as a single peak. The ultraviolet absorption spectrum of the peak was measured, and the absorption maximum was detected at 259 nm. The wavelength was the same as that of the reagent of phenyllactic acid. The resultant fraction was concentrated under reduced pressure, and the concentrate was dried under reduced pressure in a desiccator in the presence of diphosphorus pentoxide, to thereby obtain 44.4 mg of crystals of phenyllactic acid. The crystals were subjected to mass spectrometry (MS-FAB) using glycerol. (M+H)+ was detected to be 167.0, and (M+Na)+ was detected to be 188.9 by addition of NaCl. The results were the same as those of the reagent of phenyllactic acid. From the results, the phenyllactic acid concentration in the corn steep liquor was calculated to be 29.6 mg/L.

Then, the corn steep liquor was defined as a corn steep liquor itself, and L-tryptophan (Wako Pure Chemical Industries, Ltd.) was added to the corn steep liquor so as to have a concentration of 15 g/L, to thereby prepare a corn steep liquor/L-tryptophan mixture.

Production Example 4

Production Method by Partial Purification of Corn Steep Liquor Using Ion-Exchange Resin To 1 L of corn steep liquor (manufactured by Oji Cornstarch Co., Ltd.) was added 1 L of distilled water, and the resultant was adjusted to pH 7 with sodium hydroxide. The solution was passed through a strongly basic anion-exchange resin PA418 column (DIAION (registered trademark), inner diameter 45 mm×length 550 mm) converted to the formate form to adsorb phenyllactic acid, and the column was washed with 1 L of distilled water, followed by elution with 2 L of a 30% isopropanol solution containing 2 N formic acid. The eluate was concentrated to 100 mL, and the concentrate was adjusted to pH 3 with sodium hydroxide.

The concentrate was purified and analyzed in the same way as in Production Example 1, and as a result, the concentration of phenyllactic acid was found to be 747 mg/L.

Then, the corn steep liquor was defined as a corn steep liquor partially purified concentrate (concentrate), and L-tryptophan (Wako Pure Chemical Industries, Ltd.) was added to the corn steep liquor partially purified concentrate so as to have a concentration of 75 mg/L, to thereby prepare a corn steep liquor partially purified concentrate/L-tryptophan mixture.

Production Example 5

Production Method for Powder

In the same way as in Production Example 4, 5 L of a corn steep liquor partially purified concentrate/L-tryptophan mixture was prepared and spray-dried using 5 kg of bentonite powder Kunigel VA (manufactured by Kunimine Industries Co., Ltd.) as a carrier by a continuous fluidized-bed coating device FBS-0.5 (manufactured by Okawara Corporation), to thereby obtain powder.

In this case, the temperature in the device was 50° C., and the addition rate was 40 mL per minute.

Example 1

Root Promoting Effect of Phenyllactic Acid/Tryptophan Mixture by Adzuki Bean Section Immersion Treatment An aqueous solution of DL-phenyllactic acid (Sigma-Aldrich Japan) and L-tryptophan (Wako Pure Chemical Industries, Ltd.) was prepared so that the total concentration of the compounds was 400 ppm and adjusted to pH 7 with hydrochloric acid, and the solution was subjected to an adzuki bean root promotion assay (Itagaki et al. 2003. Biological activities and structure-activity relationship of substitution compounds of N-[2-(3-indolyl)ethyl]succinamic acid and N-[2-(1-naphthyl)ethyl]succinamic acid, derived from a new category of root-promoting substance, N-(phenethyl) succinamic acid analogs. Plant Soil 255: 67-75). The base of an adzuki section was immersed in the test solution for 72 hours, and adventitious roots generated 7 days after immersion were counted. The repetition number was 5.

The test was performed twice for different concentrations, and the results are shown in Tables 1 and 2.

Meanwhile, as shown in Table 3, DL-phenyllactic acid (0 and 20 ppm) and L-tryptophan (0, 400, and 1,200 ppm) were prepared, and a test was performed in the same way as above. The results are shown in Table 3.

Table 1 shows that while a slight root promoting effect was provided in the case of only DL-phenyllactic acid, the root promoting effect was drastically enhanced by mixing DL-phenyllactic acid with L-tryptophan so that DL-phenyllactic acid:L-tryptophan is 9:1 to 1:9.

Moreover, Table 2 reveals that a significant cooperation effect was obtained even when the mixing ratio of L-tryptophan to DL-phenyllactic acid was lowered to 1:99.

Moreover, Table 3 reveals that a cooperation effect was obtained even when the mixing ratio of L-tryptophan to DL-phenyllactic acid was increased to 600:1.

TABLE 1

| Concentration of L-tryptophan (ppm) | Concentration of DL-phenyllactic acid (ppm) | Number of roots | Relative value (%) |
|---|---|---|---|
| 0 | 0 | 16.4 | 100 |
| 400 | 0 | 18.6 | 113 |
| 360 | 40 | 24.8 | 151 |
| 320 | 80 | 28.2 | 172 |
| 240 | 120 | 34 | 207 |
| 160 | 240 | 48.8 | 298 |
| 80 | 280 | 55.2 | 337 |
| 40 | 360 | 54.8 | 334 |
| 0 | 400 | 22.4 | 137 |

TABLE 2

| Concentration of L-tryptophan (ppm) | Concentration of DL-phenyllactic acid (ppm) | Number of roots | Relative value (%) |
|---|---|---|---|
| 0 | 0 | 12.0 | 100 |
| 80 | 320 | 57.4 | 478 |
| 40 | 360 | 71.2 | 593 |
| 20 | 380 | 59.2 | 493 |
| 12 | 388 | 58.2 | 485 |
| 4 | 396 | 62.4 | 520 |
| 0 | 400 | 32.2 | 268 |

TABLE 3

| Concentration of L-tryptophan (ppm) | Concentration of DL-phenyllactic acid (ppm) | Number of roots | Relative value (%) |
|---|---|---|---|
| 0 | 0 | 10.8 | 100 |
| 0 | 20 | 11.6 | 107 |
| 400 | 0 | 10.6 | 98 |
| 400 | 20 | 14.8 | 137 |
| 1200 | 0 | 15.0 | 139 |
| 1200 | 20 | 20.0 | 185 |

Example 2

Comparison of Root Promoting Effect of Phenyllactic Acid/Amino Acid Mixture by Adzuki Bean Section Immersion Treatment To study the cooperation effect of phenyllactic acid and aromatic amino acids other than L-tryptophan, each of 1 mM of DL-phenyllactic acid (Sigma-Aldrich Japan), L-tryptophan (Wako Pure Chemical Industries, Ltd.), L-phenylalanine (Wako Pure Chemical Industries, Ltd.), and L-tyrosine (Wako Pure Chemical Industries, Ltd.), and aqueous solutions obtained by adding the amino acids to DL-phenyllactic acid were prepared, and subjected to the adzuki bean root promotion assay in the same way as in Example 1.

The results are shown in Table 4.

In the group of the mixture of DL-phenyllactic acid and L-tryptophan, the root promoting effect was found to increase evidently. As compared with the group treated with only DL-phenyllactic acid, the cooperation effect was provided only in the case of L-tryptophan.

TABLE 4

| Amino acid | Concentration of amino acid (mM) | Concentration of DL-phenyllactic acid (mM) | Number of roots | Ratio to untreated group (%) | Ratio to group treated with only DL-phenyllactic acid (%) |
|---|---|---|---|---|---|
| — | 0 | 0 | 14.2 | 100 | — |
| — | 0 | 1 | 18.8 | 132 | 100 |
| L-tryptophan | 1 | 0 | 19.2 | 135 | — |
| L-tryptophan | 1 | 1 | 25.8 | 182 | 137 |
| L-tyrosine | 1 | 0 | 13.6 | 96 | — |
| L-tyrosine | 1 | 1 | 16.6 | 117 | 88 |
| L-phenylalanine | 1 | 0 | 16.6 | 117 | — |
| L-phenylalanine | 1 | 1 | 17.2 | 121 | 91 |

Example 3

Root Promoting Effect of Phenyllactic Acid/Tryptophan Enantiomer Mixture by Adzuki Bean Section Immersion Treatment To compare effects of combinations of tryptophan enantiomers and phenyllactic acid enantiomers, aqueous solutions of 400 ppm of L-tryptophan, D-tryptophan (Wako Pure Chemical Industries, Ltd.), L-phenyllactic acid (Sigma-Aldrich Japan), and D-phenyllactic acid (Sigma-Aldrich Japan) were prepared. Separately, aqueous solutions of 200 ppm of each of the tryptophan enantiomers and 200 ppm of each of the phenylalanine enantiomers were prepared and subjected to the adzuki bean root promotion assay in the same way as in Example 1.

The results are shown in Table 5.

In all the combinations of enantiomers, the combination use of tryptophan and phenyllactic acid was found to provide a significant effect of enhancing the root promoting activity.

TABLE 5

| Tryptophan enantiomer [concentration] | Phenyllactic acid enantiomer [concentration] | Number of roots | Relative value (%) |
|---|---|---|---|
| — [0 ppm] | — [0 ppm] | 14.4 | 100 |
| L-form [400 ppm] | — [0 ppm] | 22.2 | 154 |
| D-form [400 ppm] | — [0 ppm] | 24.2 | 168 |
| — [0 ppm] | L-form [400 ppm] | 19.4 | 135 |

TABLE 5-continued

| Tryptophan enantiomer [concentration] | Phenyllactic acid enantiomer [concentration] | Number of roots | Relative value (%) |
|---|---|---|---|
| — [0 ppm] | D-form [400 ppm] | 27.6 | 192 |
| L-form [200 ppm] | L-form [200 ppm] | 65.6 | 456 |
| L-form [200 ppm] | D-form [200 ppm] | 59.2 | 411 |
| D-form [200 ppm] | L-form [200 ppm] | 55.8 | 388 |
| D-form [200 ppm] | D-form [200 ppm] | 50.8 | 353 |

Example 4

Root Promoting Effect of Lactic Acid Bacterium Culture/L-Tryptophan Mixture by Adzuki Bean Section Immersion Treatment The lactic acid bacterium cultures themselves and lactic acid bacterium culture/L-tryptophan mixtures obtained in Production Example 1 were separately diluted 100-fold, and the resultant solutions were subjected to the adzuki bean root promotion assay in the same way as in Example 1.

The results are shown in Table 6.

While the root promoting effects of the lactic acid bacterium cultures themselves were provided, the effects of the lactic acid bacterium culture/L-tryptophan mixtures were found to be higher evidently.

TABLE 6

| | Number of roots | Relative value (%) |
|---|---|---|
| Control (water) | 18.4 | 100 |
| FERM P-13245 strain culture | 36.4 | 198 |
| FERM P-13245 strain culture + tryptophan | 42.0 | 228 |
| FERM P-18930 strain culture | 41.2 | 224 |
| FERM P-18930 strain culture + tryptophan | 52.2 | 284 |

Culture: lactic acid bacterium culture itself
Culture + tryptophan: lactic acid bacterium culture/L-tryptophan mixture Example 5

Root Promoting Effect of Corn Lactic Acid Bacterium Culture/Tryptophan Mixture by Adzuki Bean Section Immersion Treatment The lactic acid bacterium culture of the corn meal extract itself and corn lactic acid bacterium culture/L-tryptophan mixture obtained in Production Example 2 were diluted 100-fold, and the resultant solutions were subjected to the adzuki bean root promotion assay in the same way as in Example 1.

The results are shown in Table 7.

While the root promoting effect of the corn lactic acid bacterium culture itself was provided, the effect of the corn lactic acid bacterium culture/L-tryptophan mixture was found to be higher evidently.

TABLE 7

| | Number of roots | Relative value (%) |
|---|---|---|
| Control (water) | 24.2 | 100 |
| Culture | 34.8 | 144 |
| Culture + tryptophan | 45.2 | 187 |

Culture: corn lactic acid bacterium culture itself

TABLE 7-continued

| | Number of roots | Relative value (%) |
|---|---|---|

Culture + tryptophan: corn lactic acid bacterium culture/L-tryptophan mixture

Example 6

Root Promoting Effect of Corn Steep Liquor/L-Tryptophan Mixture by Adzuki Bean Section Immersion Treatment The corn steep liquor itself and corn steep liquor/L-tryptophan mixture in Production Example 3 were subjected to the adzuki bean root promotion assay in the same way as in Example 1.

The results are shown in Table 8.

While the root promoting effect of the corn steep liquor itself was provided, the effect of the corn steep liquor/L-tryptophan mixture was found to be higher evidently.

TABLE 8

| | Dilution rate | Number of roots | Relative value (%) |
|---|---|---|---|
| Control (water) | — | 12.0 | 100 |
| Corn steep liquor | 10,000 | 14.4 | 120 |
| Corn steep liquor + tryptophan | 10,000 | 17.8 | 148 |
| Corn steep liquor | 3,000 | 18.2 | 152 |
| Corn steep liquor + tryptophan | 3,000 | 22.0 | 183 |
| Corn steep liquor | 1,000 | 22.2 | 185 |
| Corn steep liquor + tryptophan | 1,000 | 26.0 | 217 |

Corn steep liquor: corn steep liquor itself
Corn steep liquor + tryptophan: corn steep liquor/L-tryptophan mixture Example 7

CSL Purified Product+Trp Mixture Adzuki Bean Assay

Root Promoting Effect of Corn Steep Liquor Partially Purified Product/Tryptophan Mixture by Adzuki Bean Section Immersion Treatment The corn steep liquor partially purified concentrate itself and corn steep liquor partially purified concentrate/L-tryptophan mixture obtained in Production Example 4 were subjected to the adzuki bean root promotion assay in the same way as in Example 1. The results are shown in Table 9. While the root promoting effect of the partially purified product concentrate itself was provided, the effect of corn steep liquor partially purified concentrate/L-tryptophan mixture was found to be higher evidently.

TABLE 9

| | Dilution rate | Number of roots | Relative value (%) |
|---|---|---|---|
| Control (water) | — | 13.8 | 100 |
| Concentrate | 20,000 | 30.2 | 219 |
| Concentrate + tryptophan | 20,000 | 32.8 | 238 |
| Concentrate | 2,000 | 41.6 | 301 |
| Concentrate + tryptophan | 2,000 | 47.4 | 343 |

Concentrate: corn steep liquor partially purified concentrate
Concentrate + tryptophan: corn steep liquor partially purified concentrate/L-tryptophan mixture

Example 8

Effect on Lettuce Plug Seedling Raising

A hard plastic cell tray with 128 cells each having a size of 4 cm×4 cm was filled with special culture soil containing peat as a major component (Scotts, Scotts-Sierra Horticultural Products), and cabbage (variety: Calmer MR, Nitto Nosan Seed Co. Ltd.) was sown therein in a glass house and cultivated while additional fertilization was performed appropriately. On days 10 and 18 after sowing, 500 mL of a mixture of L-tryptophan and DL-phenyllactic acid diluted to predetermined concentrations in the same way as in Example 1 was sprayed. Note that deionized water was used as a control. On day 28 after sowing, 8 individuals×2 repetitions were collected, and roots were washed well with water. Then, total root lengths were measured using a root scanner (manufactured by Comair), and roots and aerial parts were dried and measured. Plant lengths and dry root weights were measured.

The results are shown in Table 10. Note that the numerals in parentheses in the table are relative values (%) with respect to the value of the control group defined as 100.

In all the treated groups, the total root lengths and dry root weights were found to increase. In the cases where the concentrations are 100 ppm or more, the total dry weights were found to increase. Therefore, the mixture was found to provide high root promoting effect in a practical seedling raising method using culture soil.

TABLE 10

| Concentration of L-tryptophan (ppm) | Concentration of DL-phenyl-lactic acid (ppm) | Total root length (m) | Dry root weight (mg) | Total dry weight (mg) |
|---|---|---|---|---|
| 0 | 0 | 8.11 (100) | 13.6 (100) | 210.0 (100) |
| 10 | 10 | 8.43 (104) | 14.1 (104) | 207.9 (99) |
| 100 | 100 | 8.92 (110) | 15.1 (111) | 218.4 (104) |
| 1000 | 1000 | 9.81 (121) | 15.2 (112) | 231.0 (110) |

Example 9

Effect of Corn Steep Liquor/Tryptophan Mixture on Broccoli Plug Seedling Raising Cultivation was performed in the same way as in Example 8 except that broccoli (variety: Ryokurei, Sakata Seed Corporation) was used as a plant. On days 9 and 18 after sowing, the corn steep liquor/L-tryptophan mixture prepared in Production Example 3 was diluted to predetermined concentrations and sprayed in an amount of 500 mL per tray. Note that deionized water was used as a control. On day 27 after sowing, 8 individuals×2 repetitions were collected, and measurement was performed in the same way as in Example 8.

The results are shown in Table 11.

In all the treated groups, the total root lengths and dry root weights were found to increase. Therefore, the mixture was found to have high root promoting effect.

TABLE 11

| Concentration of corn steep liquor + tryptophan mixture (%) | Total root length (m) | Dry root weight (mg) | Total dry weight (mg) |
|---|---|---|---|
| 0 | 11.9 (100) | 26.3 (100) | 171.5 (100) |
| 0.3 | 15.6 (131) | 32.9 (125) | 204.1 (119) |
| 1 | 16.8 (141) | 35.8 (136) | 207.6 (121) |

Example 10

Effect of Corn Steep Liquor Partially Purified Product/L-Tryptophan Mixture on Lettuce Plug Seedling Raising Lettuce was cultivated in the same way as in Example 8. On days 9 and 16 after sowing, the corn steep liquor partially purified concentrate/L-tryptophan mixture prepared in Production Example 4 was diluted 1000-fold and sprayed in an amount of 500 mL per tray. Note that deionized water was used as a control. On day 20 after sowing, 8 individuals×2 repetitions were collected, and measurement was performed in the same way as in Example 8.

The results are shown in Table 12.

In the treated groups, the total root lengths and dry root weights were found to increase. Therefore, the mixture was found to have high root promoting effect.

TABLE 12

| | Total root length (m) | Dry root weight (mg) | Total dry weight (mg) |
|---|---|---|---|
| Control group | 4.21 (100) | 5.8 (100) | 82.2 (100) |
| Treated group | 6.10 (145) | 9.9 (171) | 136.5 (166) |

Example 11

Effect of Corn Steep Liquor Partially Purified Product/Tryptophan Mixture on Melon Pot Seedling Raising Poly pots with a diameter of 9 cm were filled with culture soil "Suku-Suku Club 60" (Snow Brand Seed Co., Ltd.), and melon (rootstock cultivar Burnett, Tokai Seed Co., Ltd.) was sown and cultivated in a glass house while additional fertilization was performed appropriately. On days 11 and 21 after sowing, the corn steep liquor partially purified concentrate/L-tryptophan mixture prepared in Production Example 4 was diluted to predetermined concentrations, and the solutions were sprayed in an amount of 30 mL per pot. Note that deionized water was used as a control. On day 42 after sowing, 4 individuals×2 repetitions were collected, and measurement was performed in the same way as in Example 8.

The results are shown in Table 13. Note that the numerals in parentheses in the table are relative values (%) with respect to the value of the control group defined as 100.

In the treated groups, the total root lengths and dry root weights were found to increase. Therefore, the mixture was found to provide high root promoting effect in seedling raising using usual culture soil containing a layer of microorganisms at a high content.

TABLE 13

| | Total root length (m) | Dry root weight (mg) | Total dry weight (mg) |
|---|---|---|---|
| Control group | 25.2 (100) | 87.5 (100) | 767.4 (100) |

TABLE 13-continued

|  | Total root length (m) | Dry root weight (mg) | Total dry weight (mg) |
|---|---|---|---|
| 1000-fold diluted solution group | 28.9 (115) | 105.0 (120) | 1104.8 (144) |
| 500-fold diluted solution group | 26.9 (107) | 97.5 (111) | 1134.9 (148) |

Example 12

Effect of Treatment with Corn Steep Liquor Partially Purified Product/Tryptophan Mixture Just Before Transplantation on Paddy Rice At a farm field in Ebetsu-shi, Hokkaido, rice (variety: Nanatsuboshi) was sown on April 20 in seedling raising pots filled with culture soil for raising rice and cultivated in a plastic greenhouse. On May 23 (3 days before transplantation), the corn steep liquor partially purified concentrate/L-tryptophan mixture prepared in Production Example 4 was diluted 500-fold, and the solution was sprayed in an amount of 500 mL per tray.

On May 26, the seedlings were transplanted to the neighboring paddy using a rice transplanter (manufactured by Ando Sangyo). 14 days after transplantation, 5 seedlings×1 repetition were collected, and measurement was performed in the same way as in Example 8.

The results are shown in Table 14. Note that the numerals in parentheses in the table are relative values (%) with respect to the value of the control group defined as 100.

In the treated group, the total root lengths and dry root weights were found to increase. Therefore, the treatment just before transplantation was found to provide high effect of promoting root growth after transplantation.

TABLE 14

|  | Total root length (m) | Dry root weight (mg) | Total dry weight (mg) |
|---|---|---|---|
| Control group | 7.65 (100) | 47 (100) | 225 (100) |
| Treated group | 9.01 (117) | 58 (123) | 301 (134) |

Example 13

Effect of Corn Steep Liquor Partially Purified Product/Tryptophan Mixture Powder on Seed Corn for animal consumption (variety: Newdent 95 days DKC34-20, Snow Brand Seed Co., Ltd.) was cultivated in a test farm field in the Snow Brand Seed Co., Ltd. Hokkaido experimental farm in Naganuma-cho, Hokkaido. A basal fertilizer was applied in accordance with the fertilization standard of corn for silage, described in "Hokkaido Fertilization Guide" (Hokkaido Agricultural Policy Planning Department Edition, 2002, Hokkaido Agricultural Development and Extension Association Corporation). Seeds were coated with the powder produced in Production Example 5 at ratios of 0.3% and 0.5% with respect to the seed weight, and no treatment was performed for the control group. On May 6, the seeds were sown (distance between ridges: 66 cm×distance between plants: 22 cm). On June 23, 4 individuals×3 repetitions were collected, and measurement was performed in the same way as in Example 8.

The results are shown in Table 15. Note that the numerals in parentheses in the table are relative values (%) with respect to the value of the control group defined as 100.

TABLE 15

|  | Total root length (m) | Dry root weight (mg) | Total dry weight (mg) |
|---|---|---|---|
| Control group | 210.1 (100) | 370.0 (100) | 2132.1 (100) |
| 0.3% powder coating treated group | 230.1 (110) | 395.1 (107) | 2267.3 (106) |
| 0.5% powder coating treated group | 260.5 (124) | 425.6 (115) | 2378.9 (112) |

Example 14

Effect of Corn Steep Liquor/Tryptophan Mixture on Wheat

Wheat (variety: Hokushin) was cultivated in a farm field in Makubetsu-cho, Hokkaido. A basal fertilizer was applied in accordance with the fertilization standard of winter wheat, described in "Hokkaido Fertilization Guide" (Hokkaido Agricultural Policy Planning Department Edition, 2002, Hokkaido Agricultural Development and Extension Association Corporation). Sowing was performed on September 21 by drill sowing (distance between ridges: 30 cm), and the sowing amount was 80 kg/ha. After the ear emergence period, on June 16, June 23, and July 2 in the next year, the solutions obtained by diluting the corn steep liquor/L-tryptophan mixture prepared in Production Example 3 to predetermined concentrations, and adding polyoxyethylene hexitan fatty acid ester-containing spreading agent Approach BI (manufactured by Kao Corporation) at a concentration of 0.1% were sprayed on leaf surfaces, in particular, on ears, at a rate of 100 mL/m$^2$. The test was performed in 2 repetitions for the respective treatments. On August 5 (harvest time), collection was performed by harvesting the plant in an amount of 5 m$^2$ for the respective groups, and plant bodies were air-dried, followed by the separation of whole grains using a threshing machine. The weights of the resultant whole grains were measured to calculate the yields per unit area.

The results are shown in Table 16. Note that the numerals in parentheses in the table are relative values (%) with respect to the value of the control group defined as 100.

TABLE 16

|  | Yield (kg/ha) |
|---|---|
| Control group | 4186 (100) |
| 1,000-fold diluted solution treated group | 4353 (104) |
| 500-fold diluted solution treated group | 4688 (112) |

Production Example 6

Production Method by Lactic Acid Bacterium Culture Using Gyp Medium

Lactic acid bacteria, *Lactobacillus rhamnosus* FERM P-13245 strain and *L. plantarum* N strain, were inoculated into glucose/yeast/peptone medium (hereinafter, GYP medium, prepared by dissolving 20 g of glucose, 10 g of yeast extract, 10 g of peptone, 0.2 g of magnesium sulfate heptahydrate, 0.01 g of manganese sulfate pentahydrate, and 0.01 g of ferrous sulfate heptahydrate in 1 L of distilled water and sterilizing the solution in an autoclave at 121° C. for 15 minutes) and into a medium obtained by adding phenylalanine to GYP medium at a concentration of 9.91 g/l L (hereinafter, GYP+Phe medium), and the bacteria were cultured at 37° C. for 24 hours. The cultures were analyzed in the same way as in Production Example 1, and the phenyllactic acid concentrations in GYP medium were calculated to be 20.8 mg/L for the lactic acid bacterium *Lactobacillus rhamnosus* FERM P-13245 strain-inoculated group and 14.4 mg/L for the lactic acid bacterium *L. plantarum* N strain-inoculated group. The phenyllactic acid concentration in GYP+Phe medium was calculated to be 173.3 mg/L for the lactic acid bacterium *Lactobacillus rhamnosus* FERM P-13245 strain-inoculated group.

The liquid obtained by culturing the lactic acid bacteria in GYP medium was defined as a lactic acid bacterium culture 1, while the liquid obtained by culturing the lactic acid bacteria in GYP+Phe medium was defined as a lactic acid bacterium culture 2. In addition, a product obtained by adding L-tryptophan (Wako Pure Chemical Industries, Ltd.) to 1 L of the lactic acid bacterium cultures 1 and 2 at a concentration of 10 g/L and suspending the substance well were defined as lactic acid bacterium culture/L-tryptophan mixtures.

Example 15

Root Promoting Effect of Lactic Acid Bacterium Gyp Culture/L-Tryptophan Mixture by Adzuki Bean Section Immersion Treatment The lactic acid bacterium culture 1, the lactic acid bacterium culture 2, and the mixtures thereof with L-tryptophan obtained in Production Example 6 were diluted 100-fold, and the resultant solutions were subjected to the adzuki bean root promotion assay in the same way as in Example 1.

The results are shown in Table 17. While the root promoting effects of the lactic acid bacterium cultures themselves (culture 1 or 2) were provided, the effects of the lactic acid bacterium culture/L-tryptophan mixtures were found to be higher evidently.

TABLE 17

| | Number of roots | Relative value (%) |
|---|---|---|
| Control (water) | 15.0 | 100 |
| FERM P-13245 strain culture 1 | 23.6 | 157 |
| FERM P-13245 strain culture 1 + tryptophan mixture | 33.4 | 223 |
| FERM P-13245 strain culture 2 | 25.2 | 168 |
| FERM P-13245 strain culture 2 + tryptophan mixture | 32.0 | 213 |
| N strain culture 1 | 23.2 | 155 |
| N strain culture 1 + tryptophan mixture | 27.4 | 183 |

The invention claimed is:

1. A method of regulating plant growth, comprising applying, to a plant, phenyllactic acid or a salt thereof and tryptophan or a salt thereof.

2. A method of regulating plant growth, comprising applying, to a plant, a culture of a phenyllactic acid-producing microorganism and tryptophan or a salt thereof.

3. The method according to claim 2, wherein the phenyllactic acid-producing microorganism is a lactic acid bacterium.

4. The method according to claim 2, wherein the culture of a phenyllactic acid-producing microorganism is corn steep liquor.

* * * * *